United States Patent
Hall et al.

(10) Patent No.: US 7,993,067 B2
(45) Date of Patent: Aug. 9, 2011

(54) STRUCTURAL ARRANGEMENT FOR A FLUID-DISPENSING POWER TOOTHBRUSH

(75) Inventors: Scott E. Hall, Issaquah, WA (US); Paul Gruber, Groningen (NL); Craig Kortick Black, Bellevue, WA (US); Friedrich Stoeffler, Klagenfurt (AT)

(73) Assignee: Koninklijke Philips Electronics N.V., Eindhoven (NL)

( * ) Notice: Subject to any disclaimer, the term of this patent is extended or adjusted under 35 U.S.C. 154(b) by 584 days.

(21) Appl. No.: 11/629,823

(22) PCT Filed: Jun. 15, 2005

(86) PCT No.: PCT/IB2005/051976
§ 371 (c)(1),
(2), (4) Date: Oct. 28, 2008

(87) PCT Pub. No.: WO2005/122950
PCT Pub. Date: Dec. 29, 2005

(65) Prior Publication Data
US 2009/0136285 A1    May 28, 2009

Related U.S. Application Data

(60) Provisional application No. 60/580,657, filed on Jun. 17, 2004.

(51) Int. Cl.
*A46B 11/02* (2006.01)
(52) U.S. Cl. .................... 401/188 R; 401/282
(58) Field of Classification Search .......... 401/132–135, 401/188 R, 282; 285/148.3; 132/311
See application file for complete search history.

(56) References Cited

U.S. PATENT DOCUMENTS

| | | | | |
|---|---|---|---|---|
| 1,046,489 | A | * | 12/1912 | De Witt Pitcher ............ 248/317 |
| 4,583,563 | A | * | 4/1986 | Turner ........................... 132/311 |
| 4,876,049 | A | * | 10/1989 | Aoyama et al. ................. 264/49 |
| 5,208,933 | A | | 5/1993 | Lustig et al. |
| 5,482,086 | A | * | 1/1996 | Hori et al. ...................... 138/103 |
| 5,700,146 | A | * | 12/1997 | Kucar ............................. 433/82 |
| 5,769,553 | A | | 6/1998 | Chaudhri et al. |
| 5,993,180 | A | | 11/1999 | Westerhof et al. |
| 6,213,663 | B1 | | 4/2001 | Micaletti et al. |
| D458,027 | S | * | 6/2002 | Ferber et al. ................... D4/101 |
| 6,402,410 | B1 | * | 6/2002 | Hall et al. ...................... 401/146 |
| 6,719,471 | B1 | * | 4/2004 | Giro ......................... 401/188 R |
| 6,957,925 | B1 | * | 10/2005 | Jacobs et al. .................. 401/270 |
| 2003/0056307 | A1 | * | 3/2003 | Tybinkowski et al. ............ 15/29 |
| 2004/0062591 | A1 | | 4/2004 | Hall et al. |
| 2006/0159509 | A1 | * | 7/2006 | Grez et al. ..................... 401/123 |
| 2007/0113903 | A1 | | 5/2007 | Black |
| 2008/0137998 | A1 | | 6/2008 | Burfiend et al. |

FOREIGN PATENT DOCUMENTS

FR     2809296     11/2001

* cited by examiner

*Primary Examiner* — David J Walczak
(74) *Attorney, Agent, or Firm* — Daniel C. Sheridan (57) ABSTRACT

The fluid-dispensing power toothbrush includes a selected toothbrush architecture, generally, a handle portion, a head portion which is removable from the handle portion and a fluid-dispensing system which is removable with the head portion. The fluid-dispensing portion includes a pump and a fluid reservoir, with the reservoir being removable from the pump. The entire reservoir extends down along an exterior surface of the handle, below the lower edge of the head portion. A cover member overlies and mates with the handle, covering the reservoir when the cover member is in a closed position.

11 Claims, 8 Drawing Sheets

STRUCTURAL ARRANGEMENT FOR A FLUID-DISPENSING POWER TOOTHBRUSH

CROSS REFERENCE TO RELATED APPLICATION

This application claims the benefit of U.S. provisional application Ser. No. 60/580,657 filed 17 Jun. 2004, which is incorporated herein by reference.

This invention relates generally to fluid-dispensing teeth cleaning devices, including power toothbrushes, and more specifically concerns the physical arrangement of such a device and the relationship of its parts.

Fluid-dispensing teeth cleaning appliances, such as toothbrushes, both manual and electric, are generally well known. A large number of patents exist which cover various embodiments and features of fluid-dispensing toothbrushes. Generally, as a matter of convenience, the term "fluid-dispensing toothbrushes" herein will mean a variety of teeth cleaning appliances, including power toothbrushes, but also other teeth cleaning appliances.

Typically, such toothbrushes, and in particular electric (power) fluid-dispensing toothbrushes, which are the subject of this application, have various structural and operational disadvantages. Many such toothbrushes include a multi-use reservoir. Of these, most such reservoirs are refillable, which often results in hygiene and reliability problems. Some of the fluid-dispensing toothbrushes, usually manual, are one-piece, such that the entire unit is replaced at regular intervals. In other electric fluid-dispensing toothbrushes, where a head portion of the toothbrush containing the brushhead is removable from the handle portion and the fluid reservoir is located in the handle, the fluid-dispensing path is interrupted whenever the head portion is removed, which can create problems with continuing seal integrity and operational ease and reliability, as well as the possibility of contamination between users.

There has been no optimization of the overall configuration or length of the fluid line in such toothbrushes, which can result in operational difficulties with pumping and/or the cost/size of the pump for the device. Still further, the arrangement of controls for the toothbrush is often inconvenient, rendering difficult, if not impossible, the ability of a user to operate both the on/off control for the toothbrush and the pumping control with one hand.

The above structural disadvantages, which all generally fall into a category of "toothbrush architecture", have been a significant factor in the lack of commercial success of fluid-dispensing appliances, including fluid-dispensing toothbrushes. Accordingly, the development of an efficient and reliable fluid-dispensing toothbrush, with a specific architecture which solves the above disadvantages, would significantly assist in the commercial success of such a toothbrush.

Accordingly, the present invention in a first aspect is a fluid-dispensing power teeth cleaning appliance, comprising: a handle portion; and a head portion which includes a teeth cleaning assembly, a stem portion and a base portion, the head portion further including a fluid pathway connected to the brushhead, a fluid pump connected to the fluid pathway and a fluid cartridge, wherein the entire head portion, including the pump and the cartridge, is removable as a single unit from the handle portion.

In another aspect, the invention is a fluid-dispensing power toothbrush, comprising: a fluid-dispensing power toothbrush having bristles for brushing teeth, a first control member for dispensing fluid located on a front side of the toothbrush, facing in one direction, wherein the bristles also face in the one direction; and a second control member for on/off operation of the toothbrush on an opposing side of the handle.

Another aspect of the invention is a connecting tube for use in the fluid-dispensing power toothbrush which includes a pump element, a fluid reservoir and a fluid pathway member leading to a brushhead, from which fluid is dispensed in operation, comprising: a connecting tube member having first and second opposing end portions and an intermediate portion, the first and second end portions having a wall thickness which is sufficient to permit a reliable and solid connection with the pump and fluid pathway member, respectively, and wherein the intermediate portion is thinner walled than the end portion, to accommodate dynamic function of the fluid-dispensing system.

The invention further includes a connecting tube for a fluid-dispensing device for connection between two elements in a fluid pathway, comprising: a connecting tube member having first and second opposing ends and an intermediate portion, the first and second ends having a wall thickness which provides a strong, fluid-tight connection with the two elements, and wherein the intermediate portion is thinner walled than the ends so as to permit the intermediate portion to be bent at an angle between the first and second ends.

A further aspect of the invention is a fluid-dispensing power toothbrush having a handle portion, a head portion which is removable from the handle portion and a fluid-dispensing system which includes a fluid reservoir, a pump and a fluid pathway extending from the pump to a brushhead portion of the toothbrush, the toothbrush comprising: a fluid-dispensing toothbrush which increases in diameter in one dimension slightly over the length of the handle portion, and wherein the head portion curves from the handle portion to a substantially circular upper end which has a substantially smaller diameter than the lower end, while in an orthogonal dimension to the one dimension, one side of the handle bulges outwardly near an upper end of the handle to accommodate the pump and reservoir portions.

Figure 1:
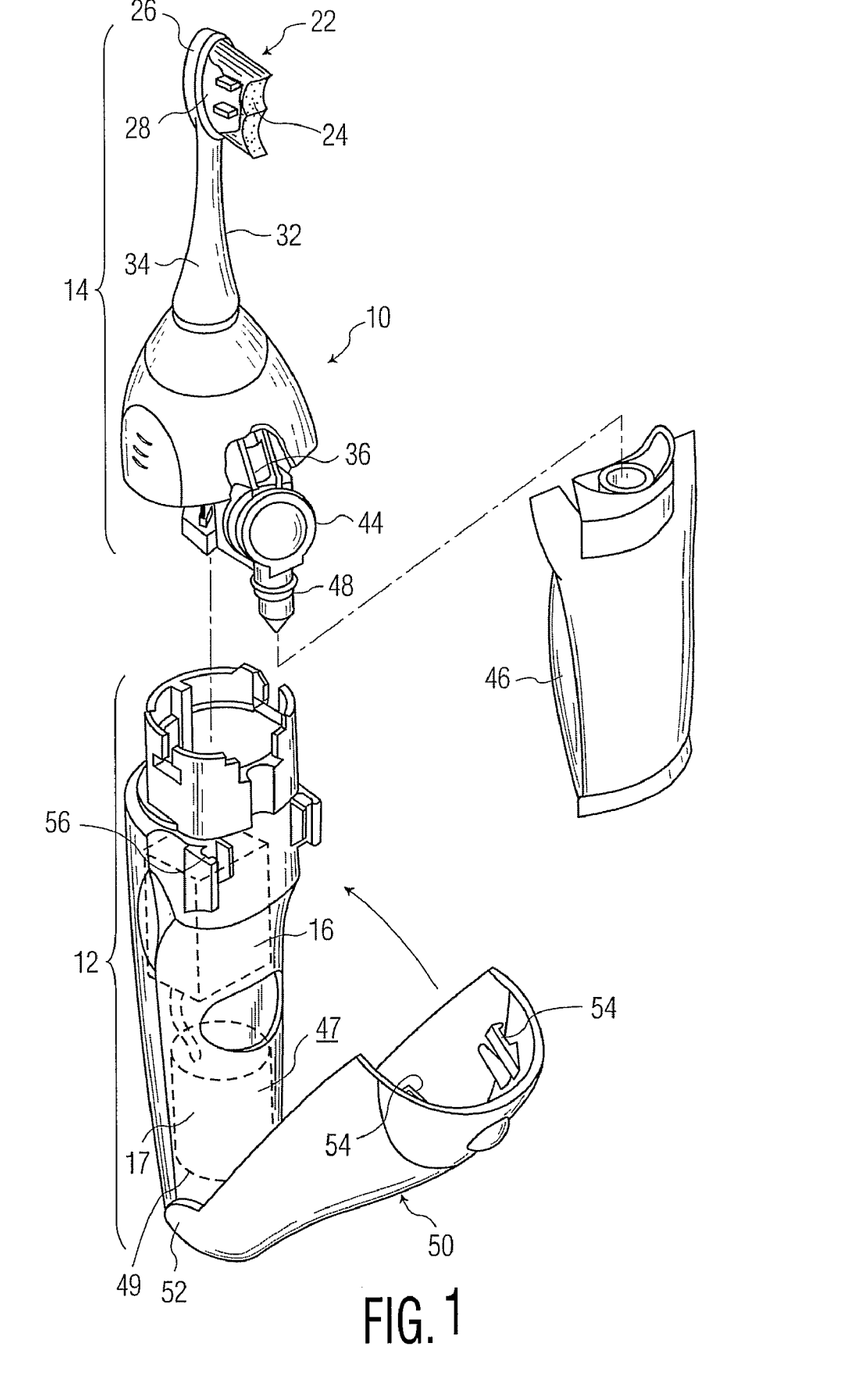
FIG. 1 is an exploded, partially cutaway, view of the fluid-dispensing toothbrush of the present invention.

FIG. 1 shows the overall architecture of the toothbrush which is the subject of this application. The fluid-dispensing power toothbrush is shown in general at 10, comprising a handle portion 12 and a head portion 14 which is removable from the handle portion. The handle portion 12 contains a drive assembly, shown generally at 16, and a rechargeable battery 17 for the drive assembly. The drive assembly can include various arrangements, including for example, various kinds of electric and electromagnetic motors, to produce the toothbrush action. One example of such an electromagnetic drive assembly suitable for use in the described embodiment is shown in U.S. Pat. No. 5,189,751. Handle portion 12 in the embodiment shown is closed, such that there is no access by the consumer to the interior of the handle.

Head portion 14 includes a conventional brushhead 22, which includes an array of bristles 24 mounted in a bristle plate 26. Bristle plate 26 has one or more openings therein to which is connected a fluid valve 28. A fluid valve structure which is useful in the present invention is a twin duckbill valve, such as shown in co-pending U.S. patent application Ser. No. 60/528,636, the contents of which are hereby incorporated by reference. The duckbill structure permits fluid to move in one direction into the bristle array under pressure but not in the other direction.

Figure 6:
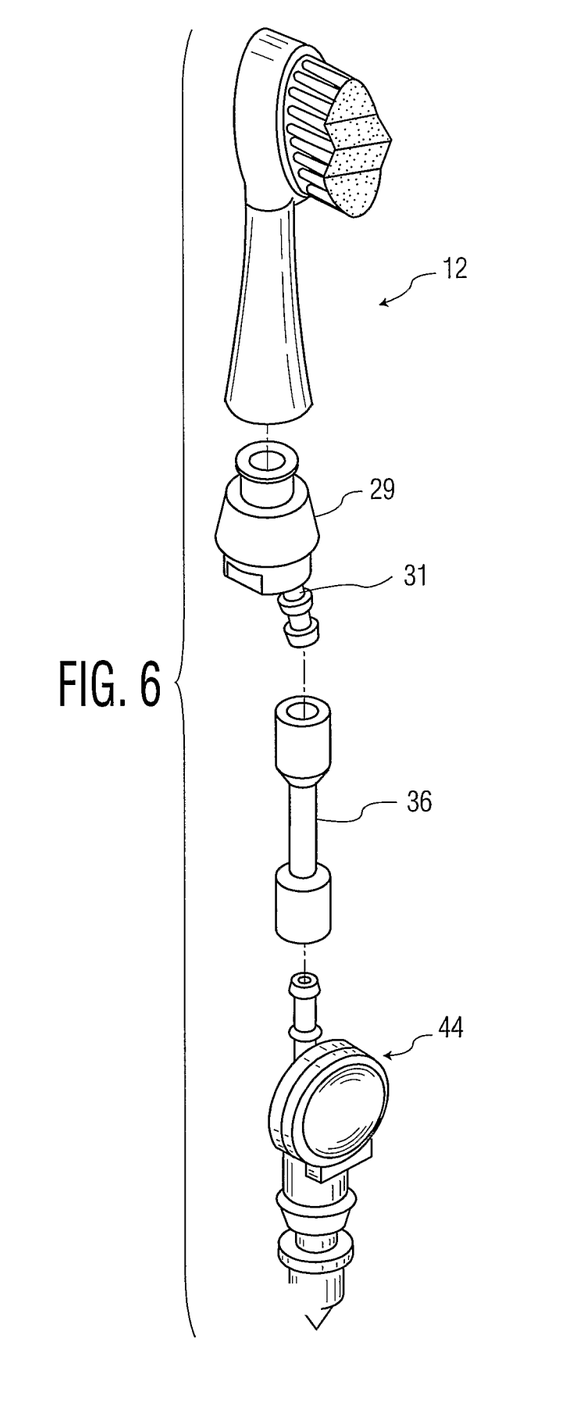
FIG. 6 is an exploded view of a fluid pathway portion of the toothbrush of FIG. 1.

Referring to FIG. 6, head portion 12 includes a hollow stem 34, through which fluid flows to the duckbill valve 28. At the lower end of the stem is a stem interface 29 having a stub 31 extending from a lower end thereof. The interface fits into the lower end of hollow stem 34 and includes an opening which extends therethrough, and through stub 31. One end of connector tube 36 is secured to hollow stub 31, while the other end of tube 36 connects to a fluid pump 44. Connector tube 36 is shown in more detail in FIGS. 2A and 2B. Pump 44 is connected to a fluid reservoir/cartridge 46, which contains the fluid to be dispensed during operation of the toothbrush. The fluid may be varied, including dentifrices, specialized medications, antibacterial or otherwise, as well as other fluids for various specific purposes. A wide variety of fluids can be used with the arrangement shown.

In the embodiment shown, the entire head portion 14, including pump 44 and reservoir 46, is removable as a unit from handle portion 12. Hence, when the brushhead itself needs to be replaced (approximately every 6 months) or for switching between users, or for cleaning, the reservoir remains with the brushhead and hence there is no interruption of the fluid path.

Cartridge 46 is conveniently removable from pump 44 without the user having to remove the entire head portion. This will occur, for instance, when the cartridge is empty. Hence, it is not necessary with the structure of the present invention that the head portion be replaced every time the cartridge is empty.

With the embodiment shown, a substantial portion of pump 44 as well as the entire cartridge 46 overlays an outer surface 47 of handle 12. Cartridge 46 extends from a lower end 48 of pump 44, which is positioned relatively close to the top of the handle, i.e. within one-half inch or so, to a point which is relatively close to the bottom 49 of the handle, i.e. within an inch or so. This arrangement permits the use of a multi-dose (use) cartridge, in this case approximately 28 uses, where each use involves approximately 15 mL of fluid. The dimensions of the cartridge can be varied to some extent to vary the capacity thereof.

Figure 2A:
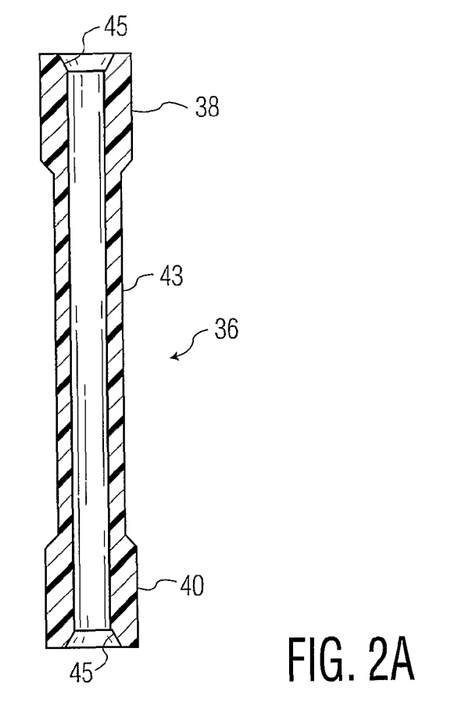
FIG. 2A is a schematic view of a portion, as manufactured, of the fluid path structure in the toothbrush of FIG. 1.
Figure 2B:
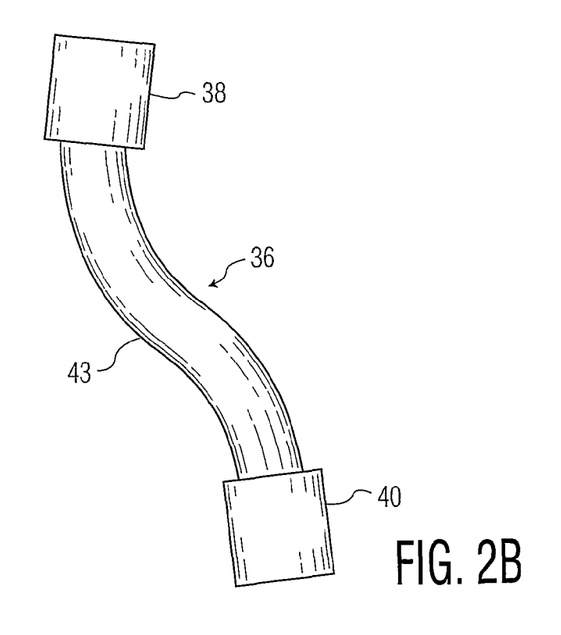
FIG. 2B shows the configuration of the part of FIG. 2A when installed

FIGS. 2A and 2B show the details of the connector tube 36 of the present invention. In the embodiment shown, the connector tube is made from a flexible plastic, such as a flexible thermoplastic elastomer and is a molded part. In FIG. 2A, the connector tube is shown straight, while in FIG. 2B, the connector tube is shown in a curved arrangement, which is its configuration in the toothbrush embodiment shown. The connector tube 36 shown herein has a total optimized length of approximately 40 mm, connecting the stem interface 29 with the top end of pump 44. The opposing end portions 38 and 40 of the connector tube have a larger diameter than intermediate portion 43. In the embodiment shown, the exterior diameter of the connector tube at the opposing end portions is approximately 6.8 mm, while the intermediate portion has an exterior diameter of approximately 3.9 mm. The internal diameter is approximately 3.3 mm at the opposing end portions and approximately 2.7 mm for the intermediate portion.

The intermediate portion 43 in the embodiment shown has a wall thickness of approximately 0.8 mm which permits this portion to flex for dynamic action, yet is strong enough to withstand the fluid pathway pressure. The end portions of the connector tube have a wall thickness of approximately 1.8 mm. The end portions provide strength for clamping. Connecting barbs on the upper end of the pump 44 and the stub 31 in the stem interface 29 assist in maintaining the connector tube in place.

The outer ends of the end portions are chamfered at 45 in the interior pathway of the tube to provide a larger "lead-in" diameter for ease of connection of the connector tube to the pump and the stub.

Pump 44 is substantially identical in basic structure to the pump shown in U.S. Pat. No. 5,993,180, the contents of which are hereby incorporated by reference. While other pump arrangements can be used to move fluid from the reservoir to the brushhead, the pump shown in the '180 patent is effective and efficient for such a purpose. The connection between pump 44 and cartridge 46 is arranged with a sharp point to enable easy penetration of cartridge 46. Further, the pump housing has been modified to permit use of pressures of up to 200 psi to handle various dentifrices.

The reservoir/cartridge 46 is, as explained above, a multi-dose (multi-use) reservoir. It includes a flexible container, allowing the reservoir to "mold" to the outer surface 47 of the handle, curving around a portion of the circumference of the handle. The cartridge 46 is conveniently removable from the pump 44, without disconnecting the pump or removing the head portion. A cartridge which is useful in the present invention is shown and described in U.S. patent application Ser. No. 60/482,914, the contents of which are also incorporated by reference herein, although it should be understood that cartridges of various configurations and arrangements can also be effectively used. The cartridge should be flexible, although a cartridge having a particular fixed configuration to fit against the curved surface of the handle could also be used.

Figure 3A:
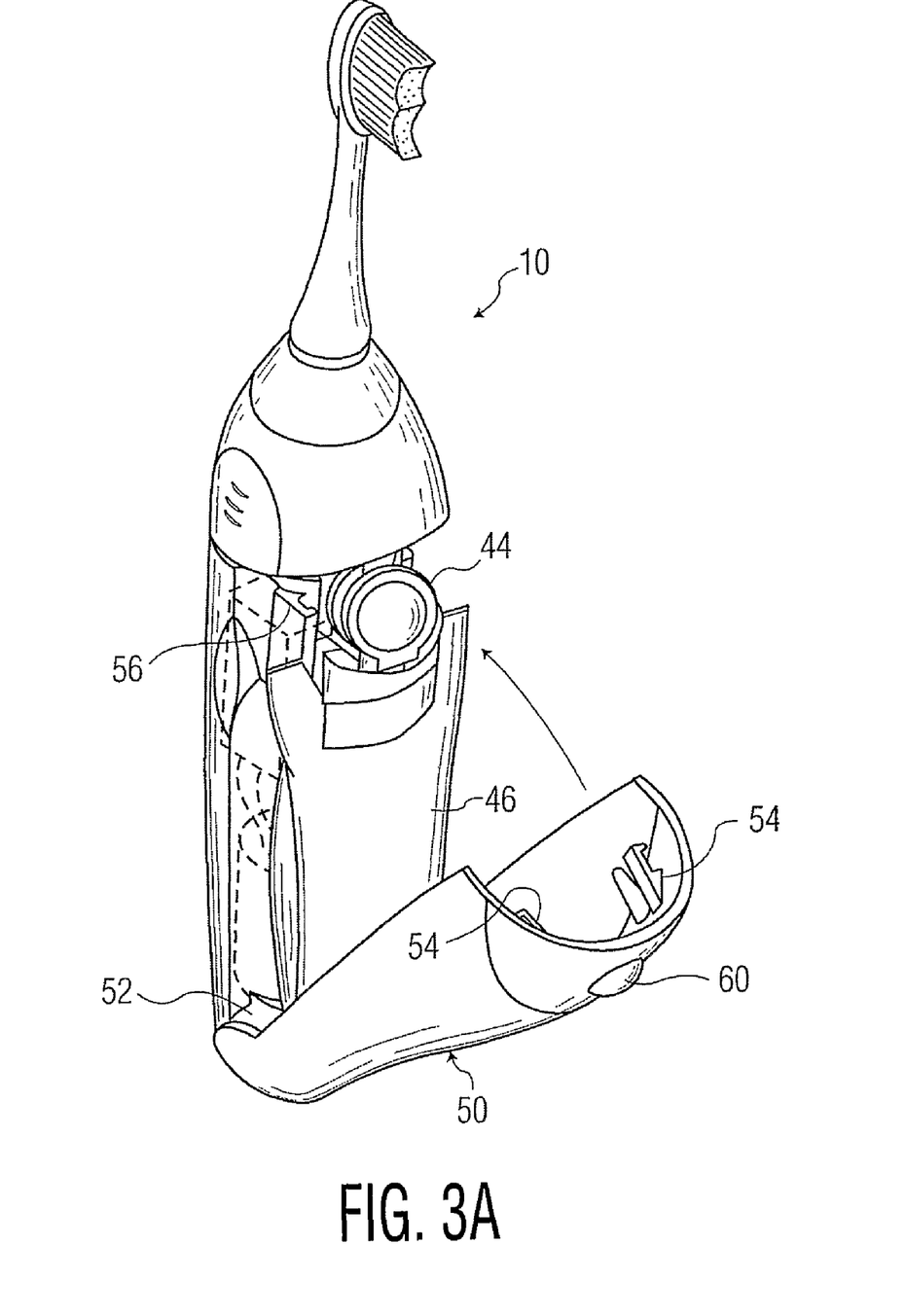
FIGS. 3A and 3B are schematic views of the cover portion of the toothbrush of FIG. 1, showing the cover in its open and closed positions relative to the handle of the toothbrush.
Figure 3B:
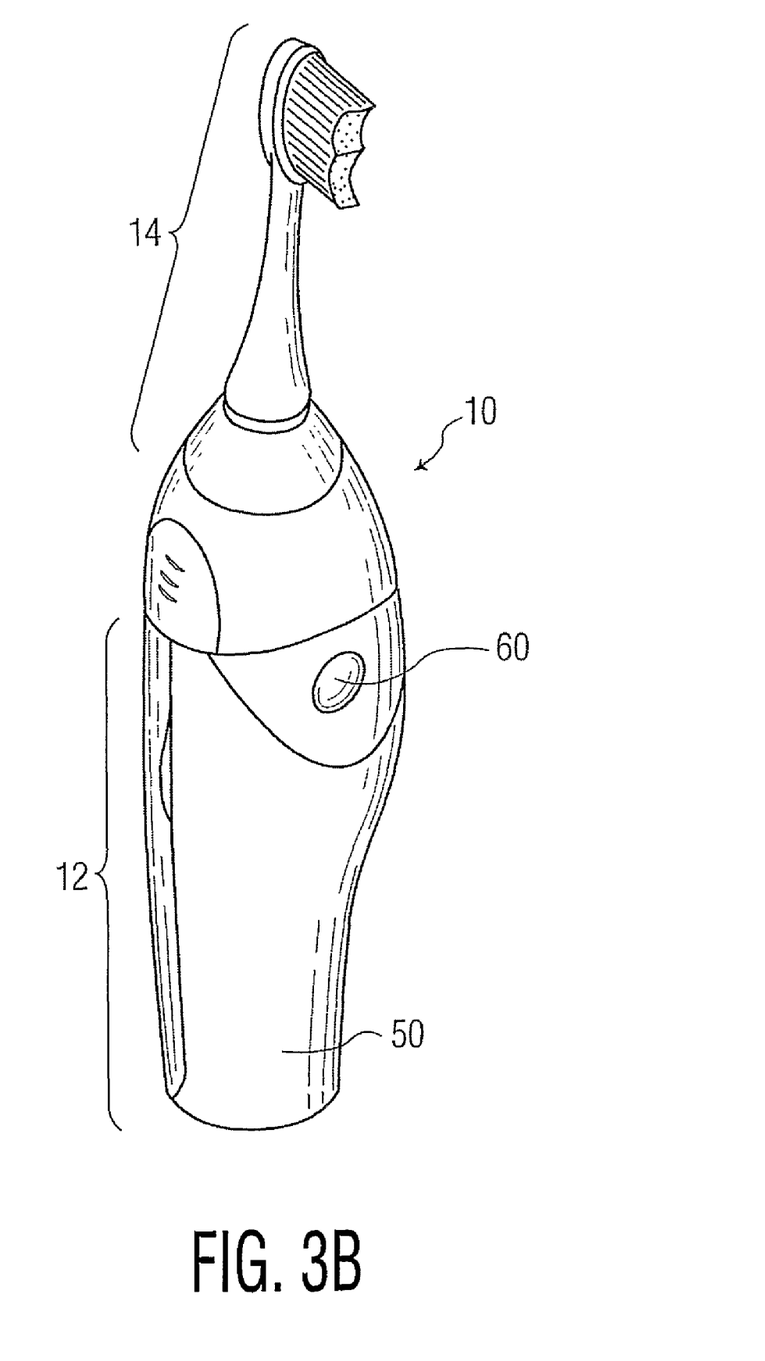

The toothbrush embodiment described herein also includes a cover member 50, which covers cartridge 46 (which lies along the outer surface of the handle as described above) and mates with the handle 12 to define a significant portion of the exterior surface of the handle. Cover 50 has pivot connection 52 at the lower end thereof, on opposing sides of the cover, in the form of small protrusions extending outwardly therefrom, which fit into corresponding openings in the handle, which allow it to swivel between closed and open positions.

Figure 5A:
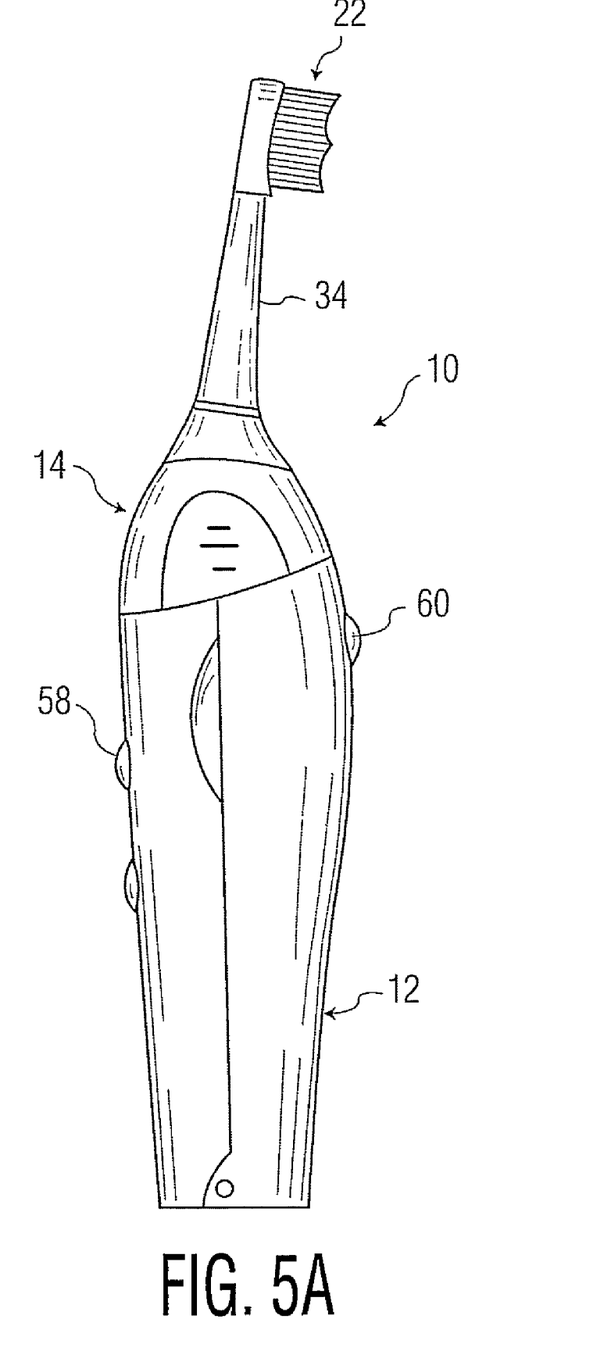
FIGS. 5A and 5B are side and front elevational views of the toothbrush of FIGS. 1-4.
Figure 5B:
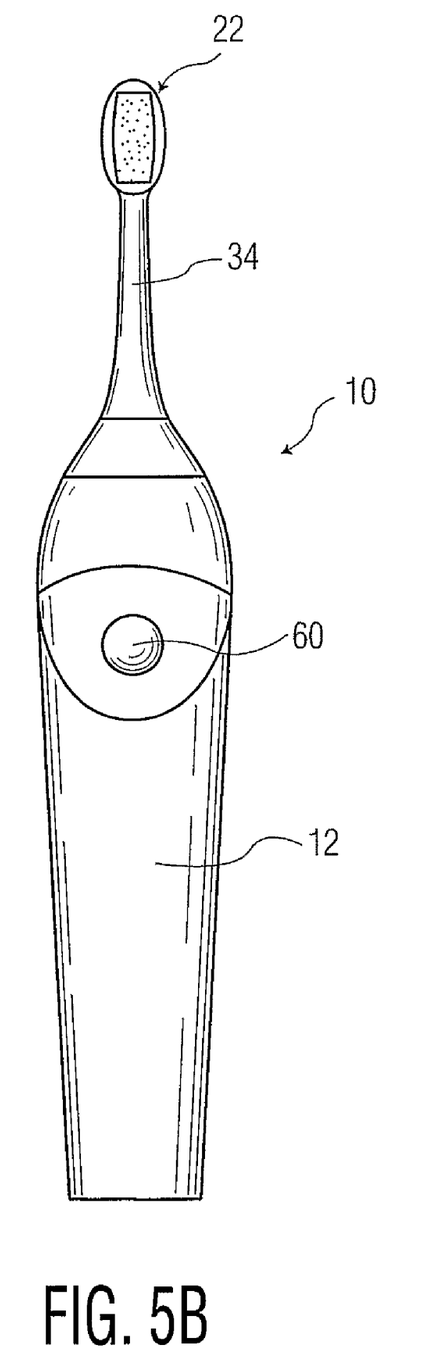

At the top of the cover 50, on the interior surface 51, are extensions 54, which fit into matching receiving portions 56 on the handle to secure the cover when it is in its closed position. Cover 50 is opened by grasping the longitudinal edges of the cover 50 near the top thereof and pulling it outwardly away from the handle, with extensions 54 separating from their mating receiving portions 56, about pivot connections 52. Cover 50 is configured to mate with the handle and the lower edge 55 of the head portion 14 to provide a symmetrical, attractive exterior appearance for the toothbrush, as shown in FIGS. 3B and 5A and 5B, while covering reservoir 46 which is positioned against the outer surface of the handle.

Figure 4:
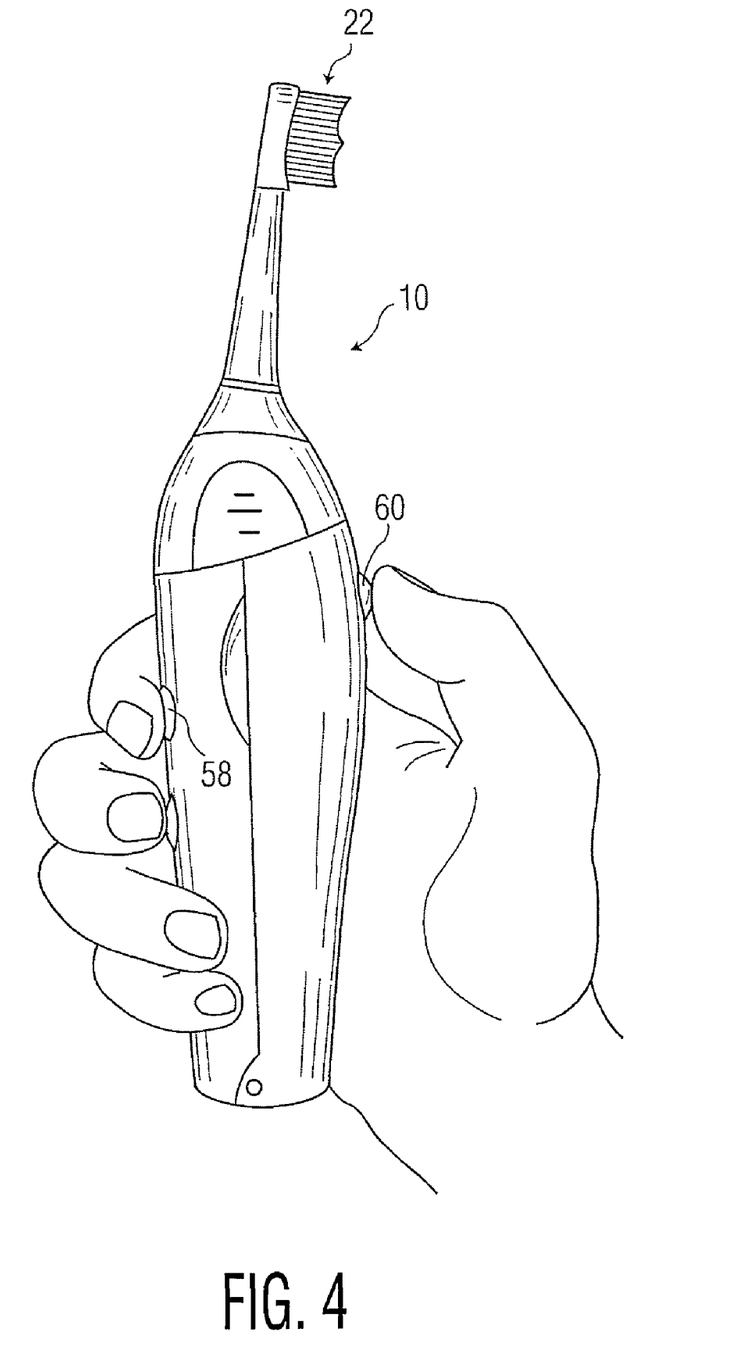
FIG. 4 is a side elevational view showing the manner in which the toothbrush is grasped in use.

In use of the toothbrush, the user grasps the toothbrush in one hand, and following actuation of an on/off control element 58, which begins operation of the toothbrush, operates pump 44 by a pump element button 60 to mechanically actuate the pump and move fluid from reservoir 46 to the brushhead. This may be done once or more at the start of brushing or may be done as needed during brushing action.

In the embodiment shown, pump control element 60 is pushed inwardly and is positioned such that it is convenient for the user to operate pump element 60 with the thumb, in one-handed operation. Pump element 60 is located on what is referred to as the front surface of the toothbrush so that it can actuate pump 44 mechanically. The brushhead extends in the same direction such that the tips of the bristles are facing toward the user, as is pump element 60, instead of facing in the opposite direction, away from the user. In the embodiment shown, pump element 60 is located approximately five inches from the lower end of handle 12, although this position can be modified.

Located on the reverse (rear facing) surface of the handle, approximately 180° from the pump control member, is on/off switch (member) 58. In the embodiment shown, on/off switch 58 is located so it can be conveniently operated by the index finger of the user, located specifically at a point slightly less than four inches from the lower end of the handle. The above arrangement of pump element 60 and on/off switch (control member) 58 has proven to be ergonomically effective and convenient for one-handed operation of the toothbrush. It provides operational control of the toothbrush with buttons located where the thumb and index finger normally are positioned when the handle is grasped.

FIGS. 5A and 5B show side and front views, respectively, of the overall toothbrush. The lower end of the toothbrush has a diameter approximately 1¼ inches and is circular in the embodiment shown. It can be a somewhat different shape than circular. The following description is of handle 12 with cover 50 closed there against, referred to as the complete handle. In one dimension, the diameter of the complete handle increases slightly from the lower end to approximately 1⅝ inches, in a generally straight line. In another dimension, orthogonal to the one dimension, the diameter of the complete handle increases gradually to a maximum of approximately two inches in the vicinity of the pump element 60, at which point the diameter decreases slightly to the upper end of the handle. The exterior surface of the complete handle is curved around its circumference. The lower edge of head portion 14 is configured to mate with the top edge of handle portion 12. The head portion decreases in dimension in both directions from the lower edge thereof to where it mates with the lower end of the stem interface 29, which is circular in the embodiment shown and has a diameter of approximately ⅝ inches. The toothbrush handle increases in diameter in the one dimension approximately 10-20% while in an orthogonal dimension to the one dimension, one side of the handle bulges outwardly near an upper end of the handle, increasing in diameter approximately 40-60%, to accommodate the pump and reservoir portions. The above configuration of the complete handle is ergonomic, easy to grasp and use.

Hence, a fluid-dispensing power toothbrush having a particular architecture has been disclosed. The architecture results in significant functional and ergonomic advantages over prior fluid-dispensing toothbrushes.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. A fluid-dispensing power teeth cleaning appliance, comprising:
    a handle portion; and
    a head portion which includes a brushhead assembly, a stem portion, a stem interface portion, a fluid pathway connected to the brushhead assembly, a fluid pump connected to the fluid pathway and a fluid cartridge, wherein the fluid pump and the fluid cartridge are positioned with the head portion, external to any housing structure of the head portion, and without a separate housing associated with and containing the fluid pump and the fluid cartridge and wherein the head portion is removable as a unit from the handle portion, leaving every other portion of the appliance in place.

2. The appliance of claim 1, wherein the cartridge includes sufficient fluid for multiple uses of the appliance.

3. The appliance of claim 1, wherein the cartridge is removable from the pump without removing the head portion from the handle portion.

4. The appliance of claim 1, wherein the cartridge and pump are arranged such that the cartridge extends entirely below a lower edge of the head portion, overlaying an outer surface of the handle portion when the head portion is operatively positioned on the handle portion.

5. The appliance of claim 1, including a pump control member located in one surface portion of the appliance, facing in one direction, with toothbrush bristles facing in the same direction and wherein an on/off member is located approximately 180° from the pump control member.

6. A fluid-dispensing power teeth cleaning appliance, comprising:
    a handle portion;
    a head portion which includes a teeth cleaning assembly, a stem portion and a base portion, the head portion further including a fluid pathway connected to the brushhead, a fluid pump connected to the fluid pathway and a fluid cartridge; and
    a cover member which extends substantially the length of the handle portion mounted to the handle for covering the pump and the cartridge against the handle in operation, and wherein when the cover is open, the entire head portion, including the pump and the cartridge, is accessible without removing the head portion from the handle portion, and is removable as a unit from the handle portion, leaving the cover member on the handle.

7. A power toothbrush which includes a fluid dispensing system, comprising:
    a power toothbrush assembly which in operation moves a brushhead in an oscillating manner;
    a pump element;
    a fluid reservoir;
    a fluid pathway member leading to the brushhead from which fluid is dispensed in operation of the power toothbrush assembly; and
    a hollow, single-piece, continuous connecting tube member, through which fluid moves from the fluid reservoir, having first and second opposing end portions and an intermediate portion integral therewith, the first and second end portions having a wall thickness which is sufficient to permit a reliable and solid connection with the pump and the fluid pathway member, respectively, and wherein the intermediate portion is thinner-walled than the end portions, to accommodate dynamic function of the fluid dispensing system and to permit the intermediate portion of the connecting tube member to be bent at an angle between the first and second ends.

8. The toothbrush of claim 7, wherein the end portions of the connecting tube are chamfered at their end openings to assist in attachment to the pump and fluid pathway member, respectively.

9. The toothbrush of claim 7, wherein the connecting tube has an internal diameter which is approximately the same over the length of the tube, except for chamfered sections at the respective ends of the tube.

10. A fluid-dispensing power toothbrush, comprising:
a handle portion;
a head portion which is removable from the handle portion; and
a fluid dispensing system which includes a fluid reservoir, a pump and a fluid pathway extending from the pump to a brushhead portion of the toothbrush, wherein the toothbrush handle increases in diameter in one dimension slightly and gradually over the length of the handle portion from a lower end to an upper end thereof, and wherein the head portion curves from the handle portion to a substantially circular upper end which has a substantially smaller diameter than the lower end thereof, while in an orthogonal dimension to the one dimension, one side of the handle bulges outwardly near an upper end of the handle, the diameter of the handle being approximately 40% to 60% greater at the bulge relative to the lower end to accommodate the pump end and reservoir portions thereof located directly therebeneath, the handle including an opening in the bulge to accommodate a pump button therethrough, wherein the handle is thus configured to be easily grasped in a hand of a user from a point near the lower end of the handle, with the user's thumb being thereby conveniently positioned to operate the pump button, while providing convenient access to the pump and the cartridge.

11. The toothbrush of claim 10, wherein the diameter of the handle increases approximately 10-20% in the one dimension.

* * * * *